United States Patent [19]

Kulkarni et al.

[11] Patent Number: 5,284,773
[45] Date of Patent: Feb. 8, 1994

[54] DETERMINATION OF LIPOPROTEIN CONCENTRATION IN BLOOD BY CONTROLLED DISPERSION FLOW ANALYSIS

[75] Inventors: Krishnaji R. Kulkarni; Jere P. Segrest, both of Birmingham, Ala.

[73] Assignee: The UAB Research Foundation, Birmingham, Ala.

[21] Appl. No.: 937,529

[22] Filed: Aug. 28, 1992

[51] Int. Cl.⁵ .............................................. G01N 35/08
[52] U.S. Cl. ........................................ 436/52; 436/45; 436/71; 422/81; 422/72
[58] Field of Search ................. 436/52, 71, 171, 45, 436/179, 180; 422/72, 81

[56] References Cited

U.S. PATENT DOCUMENTS

| | | | |
|---|---|---|---|
| 4,022,575 | 5/1977 | Hansen et al. | 436/52 |
| 4,177,677 | 12/1979 | Ruzicka et al. | 436/52 X |
| 4,314,824 | 2/1982 | Hansen et al. | 436/52 |
| 4,315,754 | 2/1982 | Ruzicka et al. | 436/52 |
| 4,399,225 | 8/1983 | Hansen et al. | 436/53 X |
| 4,520,108 | 5/1985 | Yoshida et al. | 422/81 X |
| 4,597,298 | 7/1986 | Ruzicka et al. | 73/863.71 |
| 4,742,716 | 5/1988 | Ruzicka et al. | 73/864.81 |
| 4,952,372 | 8/1990 | Huber | 436/52 X |
| 4,973,561 | 11/1990 | Hansen et al. | 422/81 X |
| 5,080,866 | 1/1992 | Petty et al. | 422/81 X |

Primary Examiner—James C. Housel
Assistant Examiner—Maureen M. Wallenhorst
Attorney, Agent, or Firm—Rhodes Coats & Bennett

[57] ABSTRACT

A continuous flow analysis system measures the cholesterol distribution among different lipoprotein classes in a blood sample. A blood plasma sample is separated into different lipoprotein classes by single vertical spin density gradient ultracentrifugation. The sample is then introduced in a continuous succession into a continuous reagent stream which flows through a detector. A signal of the reaction, such as the absorbance of the reaction product, is continuously monitored as the reaction mixture flows through the detector. The detector measures a transient signal thus allowing a relatively short reaction period. The absorbance data is digitized and analyzed with the help of a computer to generate a cholesterol profile indicative of the cholesterol concentration in each lipoprotein class.

15 Claims, 4 Drawing Sheets

DETERMINATION OF LIPOPROTEIN CONCENTRATION IN BLOOD BY CONTROLLED DISPERSION FLOW ANALYSIS

BACKGROUND OF THE INVENTION

The present invention relates generally to a method and apparatus for determining the concentrations of lipoproteins in blood using a continuous flow analyzer.

It is well-known that total serum cholesterol is strongly correlated with the incidence of atherosclerosis and coronary heart disease. More recent studies also indicate that specific fractions of cholesterol are more closely associated with coronary heart disease than others. Recent studies have implicated LDL (low density lipoprotein) as the class of lipoprotein responsible for the accumulation of cholesterol in cells, whereas HDL (high density lipoprotein) has been shown to be important in the removal of excess cholesterol from cells. Thus, increased levels of LDL cholesterol have been associated with the greater risk of coronary heart disease, while a strong inverse relationship exists between HDL cholesterol and the risk of coronary heart disease.

In addition to LDL and HDL, several other lipoproteins have been shown to represent independent risk factors for coronary heart disease. Increased plasma concentrations of lipoprotein(a) [Lp(a)], a cholesterol rich lipoprotein, has been observed in survivors of myocardial infarction. One study, which reports the relationship of levels of Lp(a) and coronary heart disease in patients who underwent coronary angiography, concluded that plasma Lp(a) appears to be a major independent coronary risk factor with an importance approaching that of LDL cholesterol or HDL cholesterol.

Increased levels of intermediate density lipoprotein (IDL) and cholesterol rich very low density lipoproteins (VLDL) are also associated with the progression of coronary heart disease. Elevation of plasma VLDL is seen in survivors of myocardial infarction, suggesting the possible involvement of this lipoprotein in the atheroschlerotic process.

Measurement of total cholesterol alone may not be adequate to identify subjects at risk for coronary heart disease. An individual with normal or near normal levels of total cholesterol may still be at risk because of low HDL levels, elevated Lp(a) levels, or elevated levels of VLDL. Moreover, the predictive power of total cholesterol for risk of coronary heart disease diminishes in men with increasing age. Therefore, assessment of the distribution of cholesterol among all the lipoproteins (a lipoprotein cholesterol profile), in addition to total cholesterol, is desirable in order to accurately assess risk for coronary heart disease.

Methods currently used to determine the concentration of cholesterol in the different lipoprotein classes can be divided into direct methods and indirect methods. In direct methods, lipoprotein cholesterol is determined by enzymatic assay of the individual lipoproteins, which are separated by ultracentrifugation, electrophoresis, or selective precipitation. The most accurate of these methods involves ultracentrifugation. However, ultracentrifugation separation methods are expensive, time-consuming, and are not practicable for clinical applications wherein multiple analyses are carried out in large numbers.

Indirect methods, as a general rule, are better suited for clinical applications than are direct methods. The most commonly used method for measurements of lipoprotein cholesterol performs multiple analyses using different aliquots of the same plasma sample. Total cholesterol (TC) is measured using a first aliquot of the sample. In a second aliquot, VLDL and LDL are removed by precipitation and the supernatant is assayed for cholesterol to provide a measure of HDL cholesterol. An estimate of VLDL is obtained by measuring the triglycerides (TG) in a third aliquot using the Friedewald formula or is measured directly after ultracentrifugal isolation of very low density lipoprotein. The LDL cholesterol concentration is not measured directly, but is calculated by subtracting the HDL cholesterol and VLDL cholesterol values from the total cholesterol.

Although this method is relatively rapid and inexpensive, there are several steps where error could be introduced. For example, accurate measurements of HDL depends on complete precipitation of apo-B containing lipoproteins. Traces of LDL in the supernatant can lead to overestimation of HDL cholesterol. Moreover, the multiple assumptions involved in the Friedewald formula make this method susceptible to error. In addition, this method does not provide a separate measure of IDL cholesterol or Lp(a) cholesterol. Instead, these values are included in the LDL cholesterol measurement.

The VAP method (Vertical Auto Profile) provides a direct method for determination of lipoprotein concentrations. The VAP method uses short spin density gradient vertical ultracentrifugation to separate the classes of lipoproteins. Analysis of cholesterol is made using an air segmented continuous flow analysis system to provide a lipoprotein cholesterol profile. The VAP method provides a direct measure of lipoprotein cholesterol using a single aliquot of plasma. However, VAP requires a relatively large sample (1.3 ml), and the equipment used in the VAP method is cumbersome, making its operation and maintenance difficult. Furthermore, this method causes overlapping of adjacent lipoprotein peaks in the cholesterol profile resulting in a substantial loss of resolution. Quantification of Lp(a) and IDL, which are not well-separated from other lipoproteins by density-gradient centrifugation becomes difficult particularly when present in small amounts.

Another method for determination of cholesterol distribution among plasma lipoproteins involves the separation of lipoproteins by high performance liquid chromotography and the on-line detection of cholesterol in the postcolumn effluent using an enzymatic reagent. This method also provides a direct measure of lipoprotein cholesterol. However, this method requires a relatively long retention period for separation of the sample. Moreover, the separation technique results in some loss of lipoproteins which could result in an underestimation of cholesterol concentration.

Accordingly, there is a need for a high rate method for direct determination of cholesterol distribution among plasma lipoproteins which is suitable for clinical applications.

SUMMARY AND OBJECTS OF THE INVENTION

The present invention is a continuous flow analysis system for direct quantitation of cholesterol in all lipoprotein classes. A blood plasma sample is placed in a tube and subjected to single vertical spin density gradient ultracentrifugation to separate the lipoproteins. The separated sample is then introduced into a continuous flow analysis system which provides a profile of the cholesterol concentrations in all lipoprotein classes.

The flow analysis system consists of a tube-piercing needle assembly, two peristaltic pumps, a flow module with a Y-shaped capillary channel for mixing sample and reagent, a Teflon coil enclosed in the temperature controlled glass chamber which functions as a reactor, a spectrophotometric detector with a microvolume flow cell, a strip chart recorder, and a computer to collect and analyze the absorbance data. One pump, for the reagent, is placed near the needle assembly and the other pump, for the reaction mixture, is placed downstream from the detector. The reagent pump provides a continuous stream of reagent which flows through the detector. Sample is drawn into the reagent by the second pump which has a higher flow rate than the first pump. The sample is continuously mixed with the reagent and is not air segmented. Dispersion is controlled by adjusting the flow rate of the reagent and sample, reducing the length and bore size of the tubing, and minimizing the total volume of the tubing to minimize convection and diffusion arising due to laminar flow. Placement of the peristaltic pump downstream from the detector further decreases dispersion.

The reaction mixture flows through a reactor consisting of a Teflon coil and to a spectrophotometric detector. The detector measures a transient signal thus allowing a relatively short retention period in the reactor. The short retention period means that a shorter reaction coil can be used thereby minimizing dispersion of the sample.

Cholesterol is continuously measured by monitoring the absorbance of the enzymatic reaction product at 505 nm as the mixture passes through the detector. The absorbance data is digitized and analyzed with the help of a computer. The absorbance curve is decomposed to make a quantitative determination of cholesterol in all lipoprotein classes.

The flow analysis system of the present invention is a highly sensitive method which requires comparatively small samples of blood and can be adapted for the analysis of lipoprotein cholesterol using fingerstick blood. Further, the method of the present invention is accurate and correlates well with other standard methods. The method is rapid enough to be used in large scale population screening. Its relatively simple instrumentation and speed make it suitable for clinical application.

Based on the foregoing, it is a primary object of the present invention to provide a rapid, simple, and relatively inexpensive apparatus for direct analysis of cholesterol in all lipoprotein classes.

Another object of the present invention is to provide a diagnostic method for direct analysis of cholesterol which is highly portable and can be performed in a doctor's office or in a patient's home.

Still another object of the present invention is to provide a diagnostic method for cholesterol testing which requires a comparatively small sample of blood and which can be used with capillary blood samples obtained from fingerstick.

Yet another object of the present invention is to provide a diagnostic method for cholesterol testing which permits direct analysis of cholesterol in all lipoprotein classes.

Other objects and advantages of the present invention will become apparent and obvious from a study of the following description and the accompanying drawings which are merely illustrative of such invention.

DETAILED DESCRIPTION OF THE DRAWINGS

Figure 1:
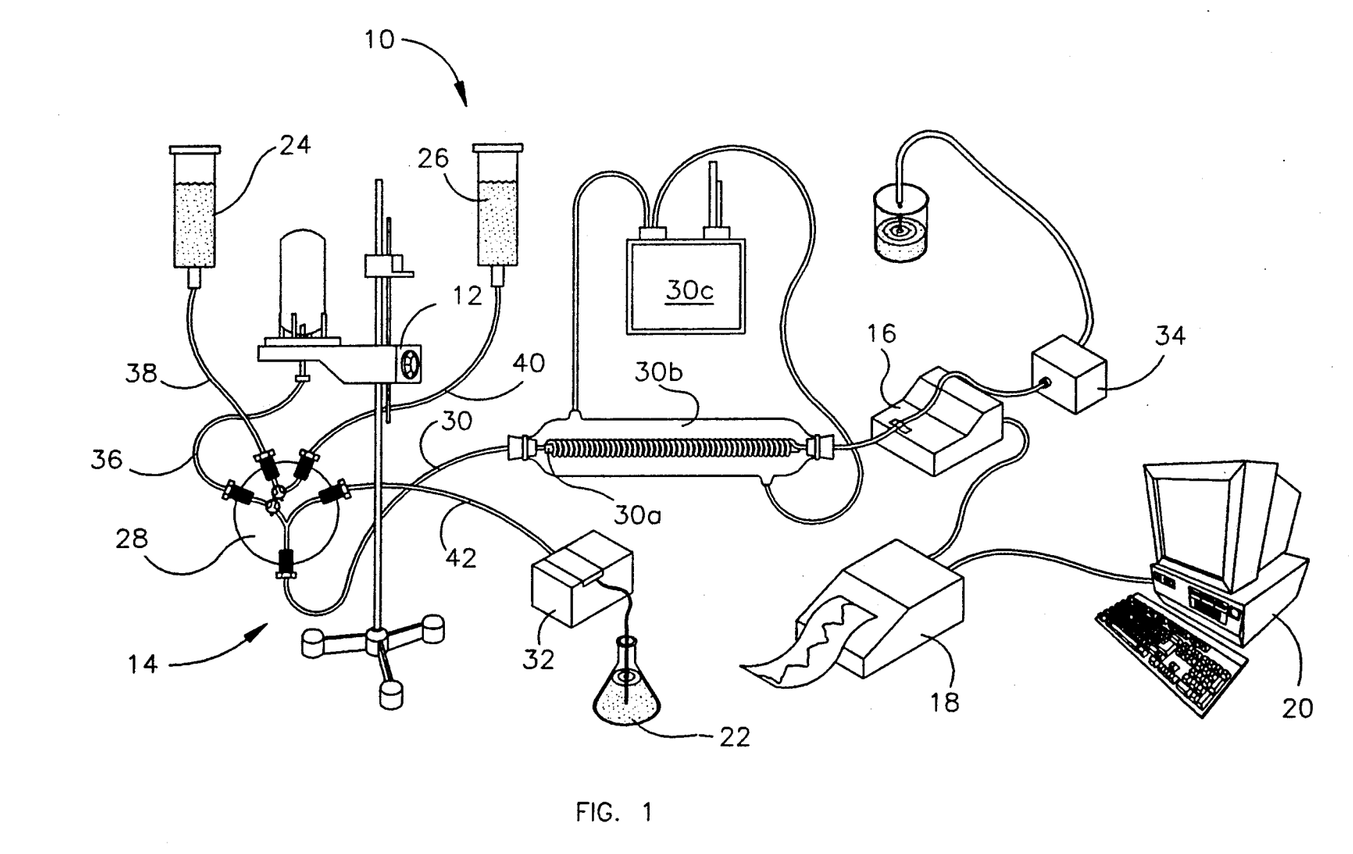
FIG. 1 is a schematic illustration of the flow analysis system of the present invention.

Referring now to the drawings, and particularly to FIG. 1, there is shown a schematic illustration of the controlled dispersion flow analysis system which is indicated generally by the numeral 10. The controlled dispersion flow analysis system 10 includes a tube-piercing needle assembly 12 for piercing a sample tube containing a sample which has been separated into individual lipoprotein classes; a flow system 14 for mixing the sample with a continuous, non-segmented reagent stream; a detector 16 for monitoring a reaction signal indicative of the cholesterol concentration in the sample; a chart recorder 18 for recording the cholesterol profile; and a computer 20 for collecting and analyzing absorbance data.

The flow system 14 includes a reservoir 22 containing a cholesterol reagent, a reservoir 24 containing a wash solution such as water, and a reservoir 26 containing a saline solution. The reservoirs 22, 24 and 26 are connected to a flow module 28 by supply tubes 42, 38 and 40 respectively. A fourth supply tube 36 connects the needle assembly 12 with the flow module 28. In the flow module 28, the sample is continuously mixed with the reagent to form a reaction mixture. The reaction mixture exits the flow module 28 through a reaction tube 30 and flows to the detector 16 which monitors a signal, such as absorbance, produced by the reaction. A first peristaltic pump 32 is disposed along the reagent supply tube 42 to provide a continuous, non-segmented stream of reagent. A second peristaltic pump 34 is disposed downstream of the detector 16 and is operated at a higher speed than the first peristaltic pump 32 to draw the sample into the flow module 28.

Figure 2:
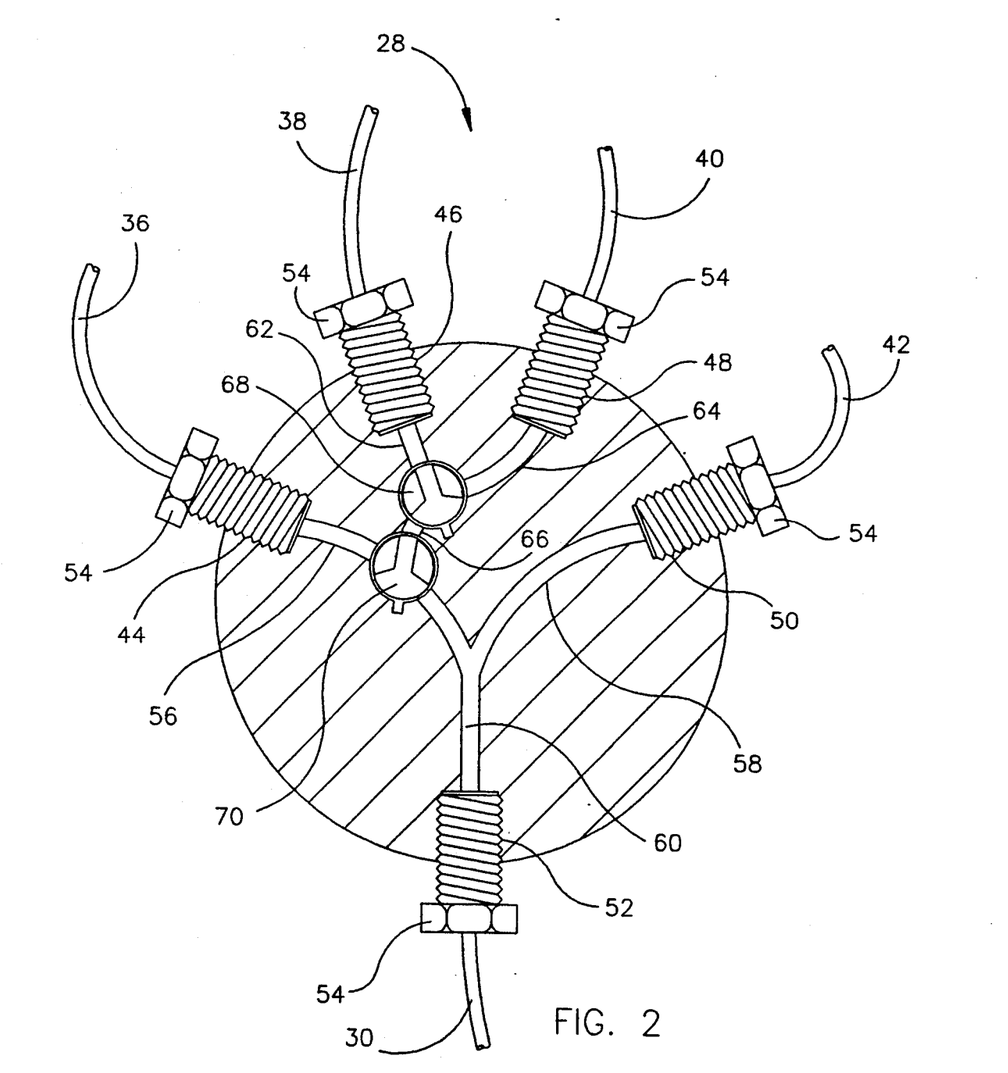
FIG. 2 is a section view of the flow module forming a part of the flow analysis system.

Referring now to FIG. 2, the flow module 28 is shown in greater detail. The flow module 28 is made of a semi-circular piece of plexiglas. The flow module 28 has four inlet ports 44, 46, 48 and 50 at the top and one outlet port 52 at the bottom. The inlet port 44 is connected by the sample supply tube 36 to the needle assembly 12. Inlet port 50 is connected by reagent supply tube 42 to the reagent reservoir 22. Capillary channels 56 and 58 extend from inlet ports 44 and 50 respectively and merge into capillary channel 60. The sample and reagent is therefore mixed at the junction of the capillary channels 56 and 58 and the mixture so formed flows through the capillary channel 60 to the outlet port 52.

The remaining two inlet ports 46 and 48 are used to deliver water and saline solution. Inlet port 46 is connected by a tube 38 to the wash solution reservoir 24, while inlet port 48 is connected by tube 40 to the saline solution reservoir 26. The capillary channels 62 and 64 extending respectively from inlet ports 46 and 48 flow into a valve 68 which permits the wash solution and saline solution to alternately flow through valve 68. The capillary channel 66 connects valve 68 to a second valve 70, which permits selection between sample and whatever solution (i.e. wash solution or saline solution) is flowing through valve 68.

The construction of the flow module 28 permits the reagent to flow through the flow module 28 at all times during the analysis, whereas sample, water and saline solution are delivered at selected points in the analysis. The two valves 68 and 70 allow the operator to switch between delivery of sample, water or saline solution at appropriate times in the analysis as will be hereinafter described.

The reaction tube 30 consists of a narrow bore Teflon tube having a plurality of coils tightly wound around a glass rod 30a. The coils are enclosed in a temperature controlled glass chamber 30b. A thermostat 30c is connected to the glass chamber 30b to maintain a temperature between approximately 35° C. and 42° C. The length and bore of the reaction tube 30 is optimized as hereinafter described to control dispersion of the sample.

The needle assembly 12, peristaltic pumps 32 and 34, and detector 16 are all commercially available products. The apparatus described herein employed a needle assembly manufactured by Beckman Instruments, peristaltic pumps 32 and 34 manufactured respectively by Brinkman Instruments and ISCO, and a spectrophotometer manufactured by LKB Pharma CF. Other manufacturer's products may also be used with equally satisfactory results.

Prior to analysis of a plasma sample, the cholesterol reagent is prepared and placed in the reagent reservoir 22. The cholesterol reagent (high-performance, Boehringr Mannheim Diagnostics) is prepared by dissolving 250 mg/ml of reagent in deionized, distilled water. Brij 35 (Sigma Chemicals) is added to the reagent solution (2.5% C/V) to facilitate lipoprotein particle breakdown. All liquid solutions, including cholesterol reagent solution, are degassed by laboratory vacuum to minimize air bubble formation.

The plasma sample is diluted with a saline/EDTA solution (0.9% NaCl, 1 mmol/l EDTA, pH=7.4, density=1.006 kg/l) and then adjusted to a density of 1.21 kg/l by adding dry KBr. A discontinuous gradient is formed in a 2 ml ultracentrifuge tube by first pipetting the saline/EDTA solution (as described above) into a glass Pasteur pipette placed in each tube and then underlaying with density adjusted plasma. The tubes are then filled and placed in a rotor and centrifuged.

Figure 3A:
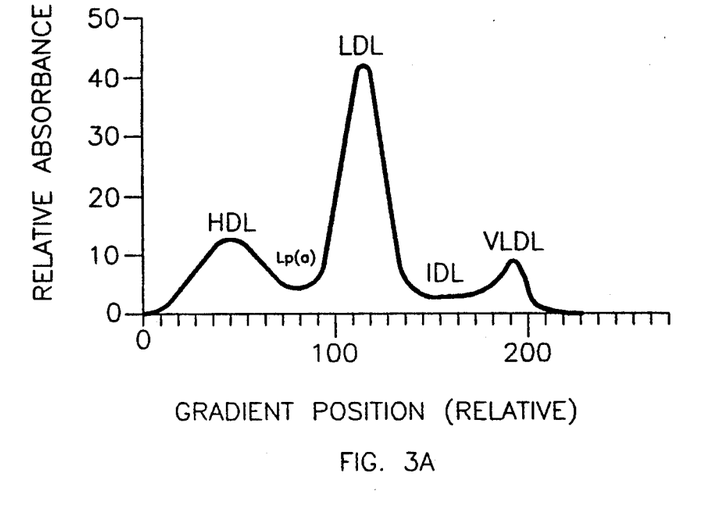
FIGS. 3A and 3B are cholesterol profiles produced as described in Example 1.
Figure 4A:
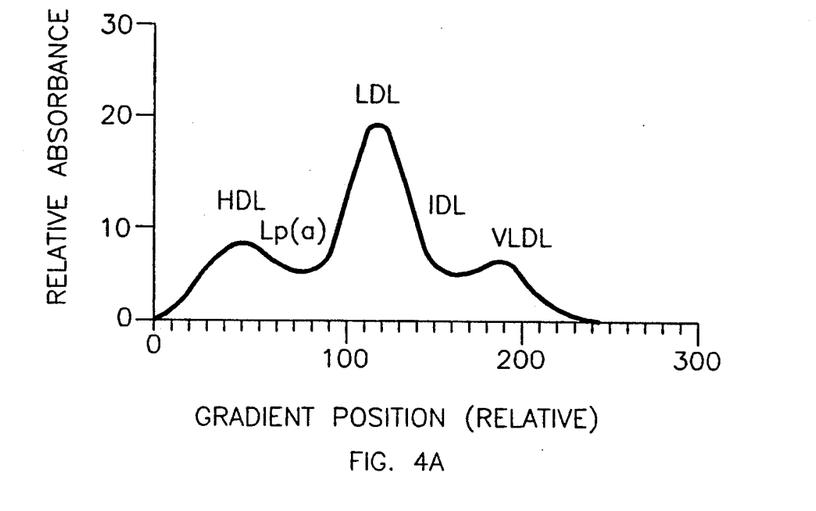
FIGS. 4A and 4B are cholesterol profiles produced as described in Example 2.

After centrifugation, the tube is placed in the needle assembly 12, the top is removed, and the tube is carefully punctured at the bottom so as not to disturb the formed gradient. The sample and reagent are drawn from their respective containers into the flow module 28 where they are mixed. The mixture of reagent and sample flows through the reaction tube 30 to the detector 16. The reaction of the sample with the reagent produces a colored reaction product. Cholesterol is measured by continuously monitoring the absorbance of this enzymatic reaction product at 505 nm as it passes through the detector 16. The chart recorder 18 records the signal measured by the detector 16 to produce a cholesterol profile while the computer 20 collects the absorbance data. A typical absorbance curve or cholesterol profile is illustrated in FIGS. 3A and 4A. Each point on the absorbance curve corresponds to the concentration of cholesterol in the corresponding position in the centrifuged sample, thus providing a profile.

At the end of each sample drain, the system is washed with water to avoid any carry-over effect. Water is used as the wash solution since it closely matches the density of the solution at the top of the sample. After washing the system, a saline solution is mixed with the reagent by switching the flow module 28 to establish a baseline for the next analysis cycle. The saline solution has a density of 1.18 which closely matches the density at the bottom of the sample and thus avoids any artifact at the baseline due to change in the absorbance caused by a change in density of the flowing solution. If a detector that does not respond to density changes is used, the use of a saline solution to establish a baseline can be eliminated. In such case, water can be used to both wash the system and to establish the baseline.

Cholesterol concentration in lipoproteins is quantified by decomposing the absorbance curve into its components using software stored in the computer's memory. The cholesterol concentration in individual lipoprotein classes is quantified based on the corresponding areas under the subcurves. The algorithm for the decomposition software has been described in prior publications. It is based on the assumption that the curve shape for an individual lipoprotein class is the same in the cholesterol profile as it is when the pre-isolated lipoprotein class is analyzed. The functional form of this curve is assumed to be a bicameral Gaussian with an exponential tail, as an originally symmetrical Gaussian peak in the centrifuged tube will be distorted by flow and mixing factors to a form that has a larger half-width on the trailing side than on the leading side and has an exponential modification to the trailing side. Location in the profile, and peak shape parameters (widths at half-height, peak height, and exponential parameter) for each lipoprotein class, are determined by isolating individual lipoproteins using preparative ultracentrifugation, then using the isolated lipoproteins in the present invention. The peak times and peak shape parameters obtained for each lipoprotein class are used to determine the area under each subcurve. Thus, cholesterol is determined by adding areas under all subcurves; as at each incident of time, total cholesterol is actually the sum of cholesterol contributions of the individual classes. A calibration plasma sample whose total cholesterol is known is included in each rotor to calibrate the area in terms of cholesterol concentration. Total cholesterol of a sample can also be determined by comparing the total area under the undecomposed curve with that of the calibration plasma.

Determination of cholesterol profile in a sample subjected to ultracentrifugation requires continuous introduction of sample into the reagent stream. Continuous introduction of the sample into the reagent stream is accomplished by the use of two peristaltic pumps. The first peristaltic pump 32, placed near the needle assembly 12, delivers a continuous stream of reagent to the flow module 28. The second peristaltic pump 34, placed downstream from the detector 16, has a higher flow rate than the first peristaltic pump 32 to continuously draw the sample into the moving reagent stream.

The two peristaltic pumps 32 and 34 control the flow rate of reagent and the flow rate of the reaction mixture (i.e., sample and reagent). Pump 34 for the reaction mixture has a higher flow rate than the pump 32 for the reagent to continuously draw the sample into the moving reagent stream. The speed of both pumps 32 and 34 are maintained constant throughout the analysis. The sample is drawn from the sample tube into the flow module 28 at a rate equal to the flow rate of the reaction mixture (i.e. rate of pump 34) minus the flow rate of reagent (i.e. rate of pump 32). The sample to reagent ratio can be adjusted by adjusting the speed of pump 34 while maintaining the speed of pump 32 constant. Alternately, the reagent to sample ratio can be adjusted by altering the speed of pump 32 while maintaining the speed of pump 34 constant.

Since there is no separation of the individual lipoprotein classes in the reaction mixture, dispersion of the sample must be closely controlled to minimize longitudinal mixing of lipoprotein fractions during analysis while allowing mixing with the reagent to achieve a measurable signal. Dispersion is governed primarily by the flow rate of the reaction mixture and reagent, and the geometry of the reaction tube 30. Smaller flow rates and smaller geometry (length and inner diameter) reduce dispersion. With smaller flow rates, convection (turbulence) of sample is reduced and radial diffusion is increased, both of which reduce dispersion. With smaller geometry, axial diffusion is reduced and radial diffusion is increased, both of which also reduce dispersion.

The similar reaction kinetics of individual lipoproteins under the conditions employed in this procedure combined with the efficient mixing of sample and reagent and the high sensitivity of the enzymatic reaction allow the measurement of a transient signal. Since the reaction does not have to reach a steady state, the length of the reaction tube can be reduced further to reduce dispersion.

For practicing the present invention the reaction tube 30 should preferably be between 1.0 m and 4.0 m in length, and most preferably be between 1.5 m and 2.0 m. The resolution increases with the decrease in reaction tube length, however, there is some loss of sensitivity due to shorter reaction time. A reaction tube length less than 1.0 m is not recommended because of poor sensitivity.

The bore size (i.e., inside diameter) of the reaction tube 30 is preferably between 0.3 mm and 1.0 mm, and most preferably between 0.5 mm and 1.0 mm. In general, resolution of the cholesterol profile improves as the diameter of the reaction tube 30 is decreased.

The flow rate of the reaction mixture should preferably be in the range of 1.00 ml/min and 2.10 ml/min. The resolution increases with a decrease in reaction mixture flow rate. This increase is accompanied by an increase in analysis time. However, the slowest flow rate does not markedly improve resolution over a slightly higher flow rate 1.56 ml/min, which provides a good compromise between optimum resolution and analysis time.

The preferred range for reagent flow rate is between approximately 0.28 ml/min and 0.94 ml/min, and most preferably between 0.5 and 0.62 ml/min. The resolution of the cholesterol profile increases with the increase in reagent flow rate. However, improvement in resolution is not constant with the change in reagent flow rate. A reagent flow rate of approximately 0.5-0.62 ml/min provides a good compromise for optimum resolution and analysis time.

Resolution of the cholesterol profile is also dependent on reagent concentration and plasma dilution. In general, the resolution of the cholesterol profile improves with the increase in reagent concentration. The sensitivity of the reaction also increases with the increase in reagent concentration. A reagent concentration in the range of 62.5 mg/ml to 312 mg/ml should be maintained, although a concentration of 250 mg/ml is most preferred.

Resolution of the cholesterol profile also increases as the plasma is diluted. A plasma dilution in the range of 10 to 50-fold provides adequate resolution and sensitivity. Dilution of the blood plasma approximately 30-fold provides the highest resolution and sensitivity.

The method of the present invention is further illustrated by the following examples:

EXAMPLE 1

Blood samples were drawn into tubes containing EDTA by venipuncture from subjects who had fasted for 12 hours. Plasma was separated by low speed centrifugation and stored at 4° C. until required for analysis.

Plasma lipoproteins were separated by single vertical spin density gradient ultracentrifugation. Prior to centrifugation, the plasma samples (50 microliters) were diluted 30-fold with 29 parts saline/EDTA solution (0.9% NaCl, 1 mmol/l EDTA, pH=7.4, density=1.006 kg/l) and then adjusted to a density of 1.21 kg/l by adding dry KBr. A density gradient was formed in 13×51 mm ultracentrifuge tubes (Beckman Instruments) by first pipetting 1.4 ml of density adjusted plasma into a Pasteur pipette placed in each tube and then carefully overlaying with 3.9 ml of saline/EDTA solution using a peristaltic pump. Tubes were sealed, placed immediately in a VTI80 (Beckman Instruments) rotor and centrifuged in an L8-80M (Beckman Instruments) ultracentrifuge. The samples were centrifuged at 80,000 rpm with a relative centrifugal field (RCF) of 462,000 gs for 31 minutes at a temperature of 20° C. An acceleration and deceleration setting of 6 was used. The total centrifugation time including deceleration was 47 minutes.

The centrifuged samples were tested using the flow analysis system described above. The operating conditions are set forth in Table 1 below.

TABLE 1

| OPERATING CONDITIONS | |
|---|---|
| Condition | Value |
| Reaction Tube | |
| Length (m) | 2.0 |
| Inside Diameter (mm) | 0.8 |
| Flow Rates (ml/min) | |
| Reagent | 0.62 |
| Reaction Mixture | 1.56 |
| Reagent Concentration (mg/ml) | 250 |
| Plasma Dilution | 30-Fold |

Figure 3B:
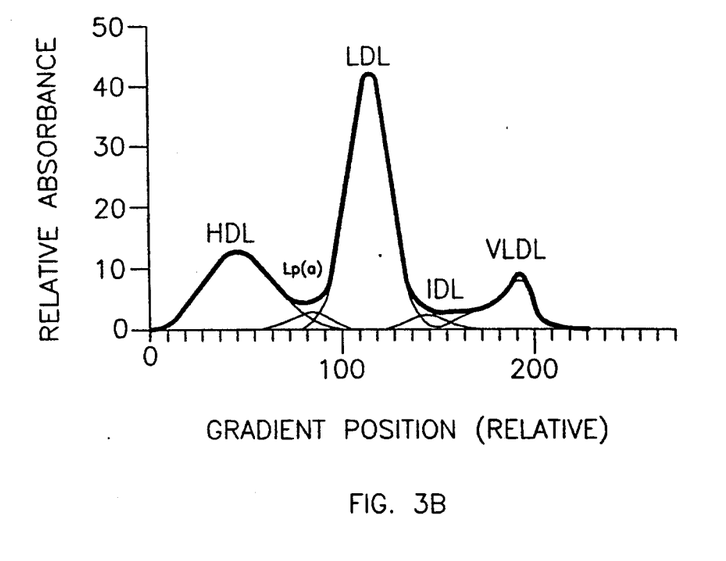

The cholesterol profile produced under operating conditions set forth in Table 1 is shown in FIG. 3A. All three major lipoprotein classes (HDL, LDL, and VLDL) were well resolved. The resolution for HDL and LDL were 74% and 94% respectively. Cholesterol in all five lipoprotein classes was quantified using the software described above. The decomposed form of the cholesterol profile is shown in FIG. 3b. Five subcurves corresponding to the five lipoprotein classes are derived from the decomposition of the absorbance curve.

The controlled dispersion flow analysis system was tested for linearity of sensitivity to cholesterol concentration and individual lipoproteins and the reproducibility of measurement within and between rotors using the conditions set forth in Table 1.

Linearity of sensitivity was determined using individual lipoprotein classes isolated from plasma samples by fixed angle preparative ultracentrifugation. Aliquots containing cholesterol concentrations from 10 to 70 mg/l were prepared by diluting individual lipoprotein classes with saline/EDTA solution. Since plasma is diluted 30-fold for analysis, this range of cholesterol corresponds to values between 300 to 2100 mg/l of lipoprotein cholesterol in undiluted plasma samples. After adjusting to a density of 1.21 kg/l, aliquots were subjected to single vertical spin density gradient ultracentrifugation using the same conditions set forth in Table 1. The sensitivity, as measured by the area under the lipoprotein peak, was linear at least up to 50 mg/l for each lipoprotein class. This corresponds to an upper limit of 1500 mg/l for individual lipoprotein classes in an undiluted plasma.

To study the reproducibility of analysis, aliquots of the sample plasma (diluted 30-fold) were analyzed in 5 rotors (7 aliquots per rotor). An aliquot of a calibration plasma with a known cholesterol concentration was also included in each rotor to calibrate the total area under the profile in terms of cholesterol concentration. The reproducibility of total cholesterol as determined by the present invention is shown in Table 2.

Northwest Lipid Research Laboratories (NWLRL) Beta Quantification Method. Venous plasma samples were collected from 23 fasting subjects for analysis. Since the Beta Quantification Method does not separate Lp(a) cholesterol and IDL cholesterol from true LDL cholesterol, LDL comparisons were made by summing Lp(a), LDL, and IDL measured by the present invention. Comparisons of HDL cholesterol, LDL cholesterol, and VLDL cholesterol are summarized in Table 3.

TABLE 3

COMPARISON OF CHOLESTEROL MEASUREMENT FOR EXAMPLE 1
WITH NWLRL METHOD (x) USING LINEAR-REGRESSION ANALYSIS

| Lipo-protein | Slope (±SD) | Intercept (±SD), mg/L | r | Sy,x | Mean NWLRL (x) | EX. 1 (y) | Difference (y − x)/x, % |
|---|---|---|---|---|---|---|---|
| Total | 0.94(0.2) | 109(37) | 0.995 | 37 | 1794(84) | 1799(79) | 0.3 |
| HDL | 0.93(0.03) | 6(17) | 0.988 | 17 | 510(24) | 481(22) | −5.6 |
| LDL | 0.92(0.03) | 138(31) | 0.991 | 42 | 1093(68) | 1140(63) | 4.2 |
| VLDL | 0.86(0.05) | 18(10) | 0.972 | 30 | 185(29) | 117(26) | −4.0 |

As shown in Table 3, the cholesterol values obtained through use of the present invention were highly correlated with those of the Beta Quantification Method. The difference between the two mean values (0.3%) for total cholesterol used in the two methods was statistically nonsignificant. HDL cholesterol and LDL cholesterol values obtained from the two methods also correlated well with the values obtained using the NWLRL Beta Quantification Method. The VLDL cholesterol values also correlated satisfactorily.

EXAMPLE 2

Venous plasma samples were collected from subjects who had fasted for 12 hours. Separation of lipoproteins by single vertical spin density gradient ultracentrifuga-

TABLE 2

REPRODUCIBILITY OF CHOLESTEROL
MEASUREMENT OF EXAMPLE 1

| | CV(%) | | | | | | |
|---|---|---|---|---|---|---|---|
| Rotor | Total | HDL | Lp(a) | LDL | IDL | LDL (NCEP)* | VDL |
| 1 | 0.72 | 1.31 | 3.44 | 1.03 | 5.97 | 1.06 | 4.0 |
| 2 | 0.48 | 1.98 | 2.99 | 1.29 | 7.21 | 0.52 | 5.08 |
| 3 | 1.12 | 2.66 | 4.06 | 1.51 | 5.31 | 0.69 | 5.96 |
| 4 | 0.57 | 2.89 | 5.49 | 2.86 | 5.21 | 1.01 | 3.95 |
| Between-rotor | 1.34 | 2.47 | 4.26 | 1.91 | 5.89 | 1.32 | 5.79 |

*Sum of Lp(a) and LDL

The coefficient of variation (CV) of total cholesterol values for aliquots within a rotor range from 0.48%–1.12%, and among all aliquots from 4 rotors was 1.34%. Thus, CV values for total cholesterol are well within the ±3% requirement of the CDC-NHLBI standardization program. The cholesterol content of individual lipoprotein classes was quantified after decomposing the cholesterol profile. As indicated by CV values in Table 2, the quantitation of lipoprotein classes by the system was also reproducible. HDL cholesterol measurements are also highly reproducible. The CV within a rotor range from 1.31%–2.89%, and between rotors was 2.47%, which is within the CDC-NHLBI Standardization Program requirement of ±6%. The reproducibility of measurement for other lipoproteins is also satisfactory.

In the absence of satisfactory reference methods for lipoprotein cholesterol measurement, the measurements taken in accordance with the present invention were compared with cholesterol values obtained by the tion was similar to that previously described, except that plasma volume was reduced. Fresh plasma samples (18 μl) were diluted 30-fold with saline/EDTA solution and then adjusted to a density of 1.21 kg/l by adding dried KBr. A discontinuous gradient was formed in 2 ml ultracentrifuge tubes (Beckman Instruments) by first pipetting 1.35 ml saline/EDTA solution into a glass Pasteur pipette placed in each tube and then underlaying with 0.55 ml of density adjusted plasma. Tubes were sealed and placed immediately in a Beckman TLV-100 rotor (which holds eight tubes), and centrifuged in a Beckman TL-100 tabletop centrifuge at 100,00 rpm for 22 minutes (excluding deceleration time) at 20° C. using acceleration and deceleration settings of 5.

The plasma sample was analyzed using the controlled dispersion flow analysis system described above. The operating conditions for this test are set forth in Table 4.

TABLE 4

OPERATING CONDITIONS

| Condition | Value |
| --- | --- |
| Reaction Tube | |
| Length (m) | 1.5 |
| Inside Diameter (mm) | 0.8 |
| Flow Rates (ml/min) | |
| Reagent | 0.5 |
| Sample | 0.6 |
| Reaction Mixture | 1.1 |
| Reagent Concentration (mg/ml) | 250 |
| Plasma Dilution | 30-Fold |
| Temperature (°C.) | 37 |

Figure 4B:
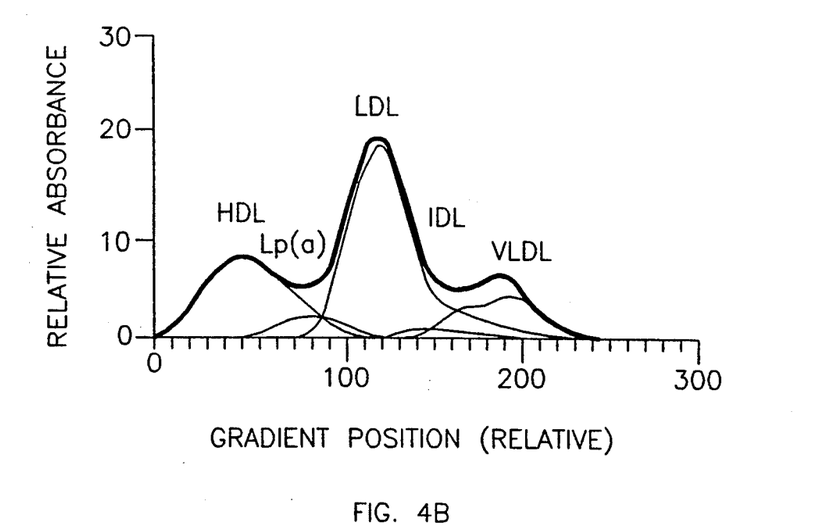

The cholesterol profile using the conditions described above is shown in FIG. 4A and 4B. While there is some loss of resolution as compared to Example 1, HDL, LDL and VLDL peaks are all adequately resolved. Further, the method of Example 2 used a much smaller sample and required less time for analysis. The time required to analyze eight centrifuged samples was approximately 30 minutes (including delay time between tubes), compared to 55 minutes for Example 1. The sample size (18 µl) makes the method of Example 2 suitable for use with fingerstick blood. Lipoprotein peaks in the profiles obtained from a single plasma were highly reproducible.

The method of Example 2 was also tested for linearity of sensitivity, reproducibility of results and correlation with the NWLRL Beta Quantification Method. The procedures used were the same as described in connection with Example 1. The integrated peak areas in each aliquot were found to be linear at least in range of 10.0 through 60.0 mg/l cholesterol. Since plasma samples were diluted 30-fold for analysis, this corresponds to an upper limit of 1800 mg/l cholesterol in each lipoprotein class. The reproducibility of the cholesterol profile for the method of Example 2 is shown in Table 5.

TABLE 5

REPRODUCIBILITY OF CHOLESTEROL MEASUREMENT OF EXAMPLE 2

| | CV(%) | | | | |
| --- | --- | --- | --- | --- | --- |
| Rotor | Total | HDL | LDL | LDL (NCEP)* | VLDL |
| 1 | 1.85 | 2.50 | 1.60 | 2.50 | 6.20 |
| 2 | 1.65 | 2.80 | 1.90 | 1.60 | 6.50 |
| 3 | 3.15 | 3.00 | 2.20 | 2.50 | 11.20 |
| 4 | 1.35 | 2.00 | 2.60 | 1.00 | 5.00 |
| 5 | 1.85 | 1.90 | 1.40 | 1.60 | 9.80 |
| Inter-rotor | 2.45 | 3.40 | 2.75 | 2.00 | 8.60 |

*Sum of Lp(a), IDL and LDL

The coefficient of variation of total cholesterol values for aliquots in a rotor range from 1.35 to 3.15%, and among all aliquots from 5 rotors was 2.45%. The cholesterol content of individual lipoprotein classes was quantified after decomposing the cholesterol profile as described above. The quantitation of lipoprotein classes was also highly reproducible. Somewhat higher CV values in the case of VLDL cholesterol were due to the low VLDL cholesterol concentrations (90 mg/l) in the plasma sample used in this experiment.

The values obtained using the method described in Example 2 also correlated well with the NWLRL Beta Quantification Method. The result of linear regression analysis comparing the two methods is set forth in Table 6.

TABLE 6

COMPARISON OF CHOLESTEROL MEASUREMENT FOR EXAMPLE 2 WITH NWLRL METHOD (x) USING LINEAR-REGRESSION ANALYSIS

| Lipo-protein | Slope (±SD) | Intercept (±SD), mg/dL | r | Sy,x mg/L | Mean NWLRL | EX. 2 (y) | Difference (y − x)/x, % |
| --- | --- | --- | --- | --- | --- | --- | --- |
| Total | 0.95(0.03) | 94(49) | 0.992 | 50 | 1802 ± 84 | 1805 ± 81 | 0.2 |
| HDL | 0.91(0.04) | 4(19) | 0.983 | 20 | 498 ± 23 | 455 ± 21 | −8.6 |
| LDL | 0.93(0.03) | 157(36) | 0.988 | 50 | 1110 ± 70 | 1190 ± 66 | 7.2 |
| VLDL | 0.93(0.04) | −8(10) | 0.978 | 28 | 187 ± 29 | 165 ± 28 | −11.8 |

The measurements taken in accordance with Example 2 were highly correlated with those of the NWLRL Beta Quantification Method.

The present invention provides a highly sensitive new method for direct measurement of cholesterol in all lipoprotein classes. Since the present invention is capable of measuring cholesterol using only 18 micro liters of plasma, it can be adapted for the analysis of lipoprotein cholesterol using fingerstick blood. The method of the present invention is accurate, reproduceable and correlates with other standard methods. Further, the present invention is rapid and less labor intensive than other direct methods of cholesterol measurement making it suitable for clinical applications. The continuous profile provided by the present invention allows more precise determination of the nature of lipid abnormalities than can be seen by conventional methods, and allows direct comparisons of two profiles.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A flow analysis method for measuring, in a blood sample containing a plurality of lipoprotein classes, the distribution of cholesterol among said lipoprotein classes comprising:

a) separating the blood sample into two or more fractions representing different lipoprotein classes to form a gradient;

b) providing a continuous, non-segmented stream of reagent which continuously flows from a reagent source to a detector;

c) introducing each sample fraction in said gradient into the reagent stream in a continuous succession upstream from the detector;

d) reacting each sample fraction with the reagent as the sample fractions flow toward said detector to produce a measurable reaction signal indicative of the cholesterol concentration in each sample fraction of the gradient while controlling dispersion of the sample fractions within the reagent stream;

e) continuously measuring each reaction signal at said detector before each reaction is completed and while each reaction signal is in a transient state; and f) recording each reaction signal to produce a continuous cholesterol profile including each lipoprotein class.

2. The flow analysis method of claim 1 wherein the step of separating the blood sample into two or more fractions includes centrifuging the blood sample to form a density-gradient.

3. The flow analysis method of claim 1 wherein the step of introducing the sample fractions in said gradient into the reagent stream comprises operating a first pump for the reagent at a first predetermined flow rate, and operating a second pump for the mixture of sample and reagent at a second predetermined flow rate which is higher than the first predetermined flow rate.

4. The flow analysis method of claim 1 further including the step of diluting the blood sample prior to the separating step.

5. The flow analysis method of claim 4 wherein the blood sample is diluted with a saline solution by a 10 to 30 fold dilution.

6. The flow analysis method of claim 1 wherein the step of reacting each sample fraction with the reagent includes passing the mixture of each sample fraction and reagent through a tube of predetermined length and inside diameter to minimize dispersion of the sample fractions.

7. The flow analysis method of claim 6 wherein the tube has a length of between 1 m and 3 m.

8. The flow analysis method of claim 7 wherein the tube has a inside diameter of between 0.3 mm and 1.0 mm.

9. The flow analysis method of claim 1 wherein the the absorbance of the reaction signals are continuously measured.

10. The flow analysis method of claim 9 wherein the absorbance of each reaction signal is measured by a spectrophometric detector.

11. A flow analysis method for measuring, in a blood sample containing a plurality of lipoprotein classes, the distribution of cholesterol among said lipoprotein classes comprising:

a) forming a sample gradient by separating the blood sample into two or more sample fractions representing different lipoprotein classes;

b) providing a continuous, non-segmented reagent stream which continuously flows from a reagent stream source to a detector by operating a first pump for the reagent at a first predetermined flow rate;

c) introducing each sample fraction in said gradient into the reagent stream by operating a second pump located downstream from the first pump at a higher flow rate than the first pump so as to induce the sample gradient into the reagent stream in a continuous succession;

d) reacting each sample fraction in the sample gradient with the reagent while controlling dispersion of the sample fractions to produce a measurable reaction signal indicative of the cholesterol concentration in each sample fraction; and e) producing a continuous profile of the cholesterol concentration in each sample fraction by continuously monitoring each reaction signal as the sample fractions in the reagent stream pass through the detector.

12. The flow analysis method of claim 11 wherein the step of separating the blood sample into two or more sample fractions includes centrifuging the blood sample to form a density gradient.

13. The flow analysis method of claim 11 further including the step of diluting the blood sample prior to the separating step.

14. A flow analysis system for determination of cholesterol distribution among plasma lipoproteins, comprising:

a) separating means for separating a plasma sample into two or more lipoprotein fractions to form a sample gradient;

b) a first pump for providing a continuous, non-segmented stream of reagent during analysis of the sample gradient;

c) a second pump located downstream of the first pump and operated at a higher flow rate than the first pump for continuously introducing the sample gradient into the reagent stream such that each of the lipoprotein fractions enters the reagent stream in a continuous succession, d) a reactor located between the first pump and the second pump for reacting the lipoprotein fractions with the reagent as the lipoprotein fractions flow through the reactor to produce a measurable reaction signal indicative of the cholesterol concentration in each of the lipoprotein fractions;

e) a detector disposed in the reagent stream downstream of the reactor for sensing each reaction signal as the lipoprotein fractions flow through the detector and while each reaction signal is in a transient state; and f) recording means operatively connected with said detector for recording each reaction signal to form a cholesterol profile indicative of the cholesterol concentration in each lipoprotein fraction.

15. The flow analysis system of claim 14 wherein the separating means comprises a centrifuge.

* * * * *